United States Patent [19]

Hasegawa

[11] Patent Number: 4,908,844
[45] Date of Patent: Mar. 13, 1990

[54] APPARATUS FOR DETECTING ERROR OF DETECTOR

[75] Inventor: Shinji Hasegawa, Ootawara, Japan

[73] Assignee: Kabushiki Kaisha Toshiba, Kawasaki, Japan

[21] Appl. No.: 173,816

[22] Filed: Mar. 28, 1988

[30] Foreign Application Priority Data

Mar. 31, 1987 [JP] Japan .................................. 62-75873

[51] Int. Cl.$^4$ ................................................ A61B 6/04
[52] U.S. Cl. ........................................ 378/209; 269/322
[58] Field of Search ............... 378/208, 209, 177, 179, 378/180, 195, 196; 250/342; 369/322; 324/160

[56] References Cited

U.S. PATENT DOCUMENTS

| 3,822,875 | 7/1974 | Schmedemann | 378/209 |
| 4,019,059 | 4/1977 | Brundin | 378/209 |
| 4,481,657 | 11/1984 | Larsson | 378/209 |
| 4,618,133 | 10/1986 | Siczek | 378/209 |
| 4,650,172 | 3/1987 | Wathelet | 378/209 |
| 4,665,369 | 5/1987 | Faller et al. | 324/326 |
| 4,694,172 | 9/1987 | Powell et al. | 250/342 |
| 4,697,081 | 7/1987 | Baker | 250/342 |
| 4,704,533 | 11/1987 | Rose et al. | 250/342 |
| 4,712,372 | 12/1987 | Dickey et al. | 324/160 |
| 4,731,889 | 3/1988 | Ishikawa | 378/209 |
| 4,783,631 | 11/1988 | Nakashima et al. | 324/160 |

FOREIGN PATENT DOCUMENTS

| 3044688 | 7/1982 | Fed. Rep. of Germany . |
| 3219923 | 12/1982 | Fed. Rep. of Germany . |
| 3344647 | 6/1985 | Fed. Rep. of Germany ...... 378/209 |

Primary Examiner—Craig E. Church
Attorney, Agent, or Firm—Oblon, Spivak, McClelland, Maier & Neustadt

[57] ABSTRACT

In order to detect a rise angle of a bed of an X-ray fluoroscopic imaging system, first and second potentiometers of the identical characteristic are respectively connected to a sprocket for rotating a sector gear to raise the bed and a tension roller which is rotated in synchronism with rotation of the sprocket through a chain. Outputs from the first and second potentiometers are input to a differential amplifier to calculate a difference therebetween. It is determined by a window comparator whether or not the difference falls within a predetermined allowable range. When the difference falls outside the predetermined allowable range, an error is detected. The outputs from the first and second potentiometers are input to minimum and maximum voltage detection comparators. It is checked whether or not the output itself from the potentiometer falls within a predetermined output range. If the output falls outside the predetermined output range, an error is detected.

8 Claims, 4 Drawing Sheets

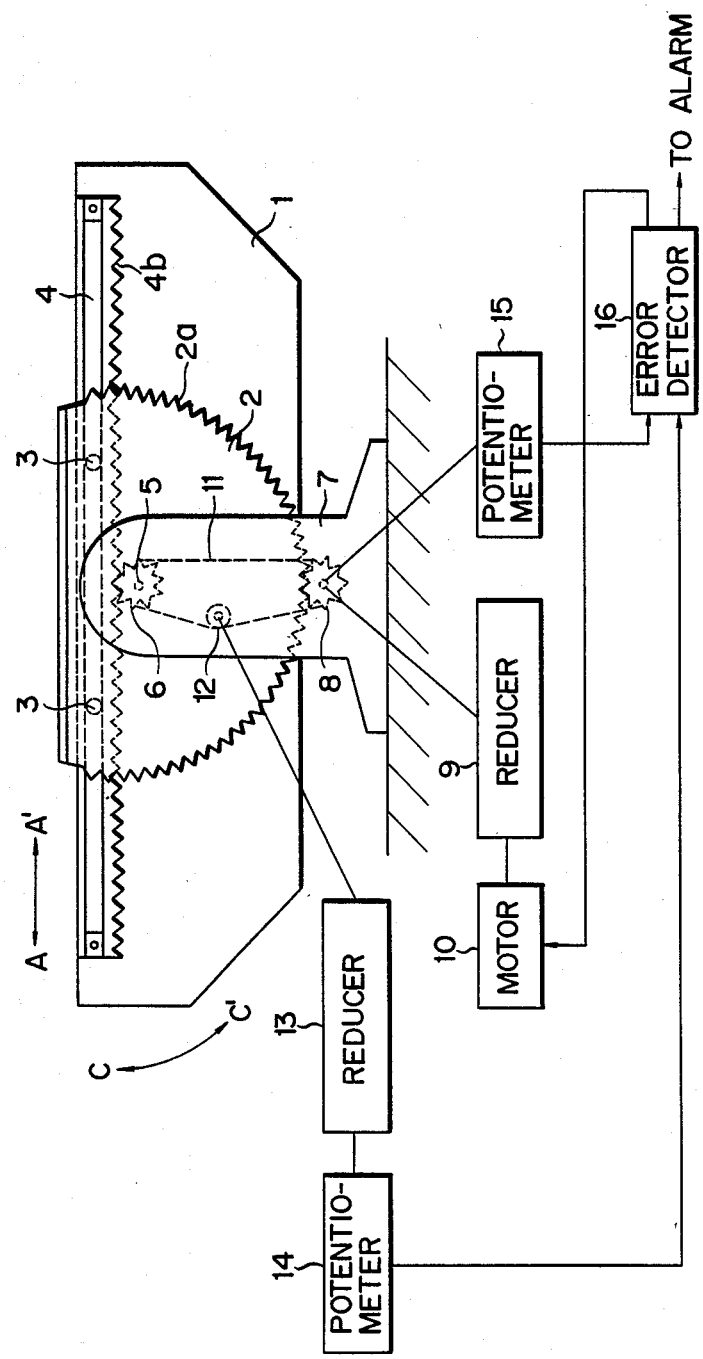
F I G. 2

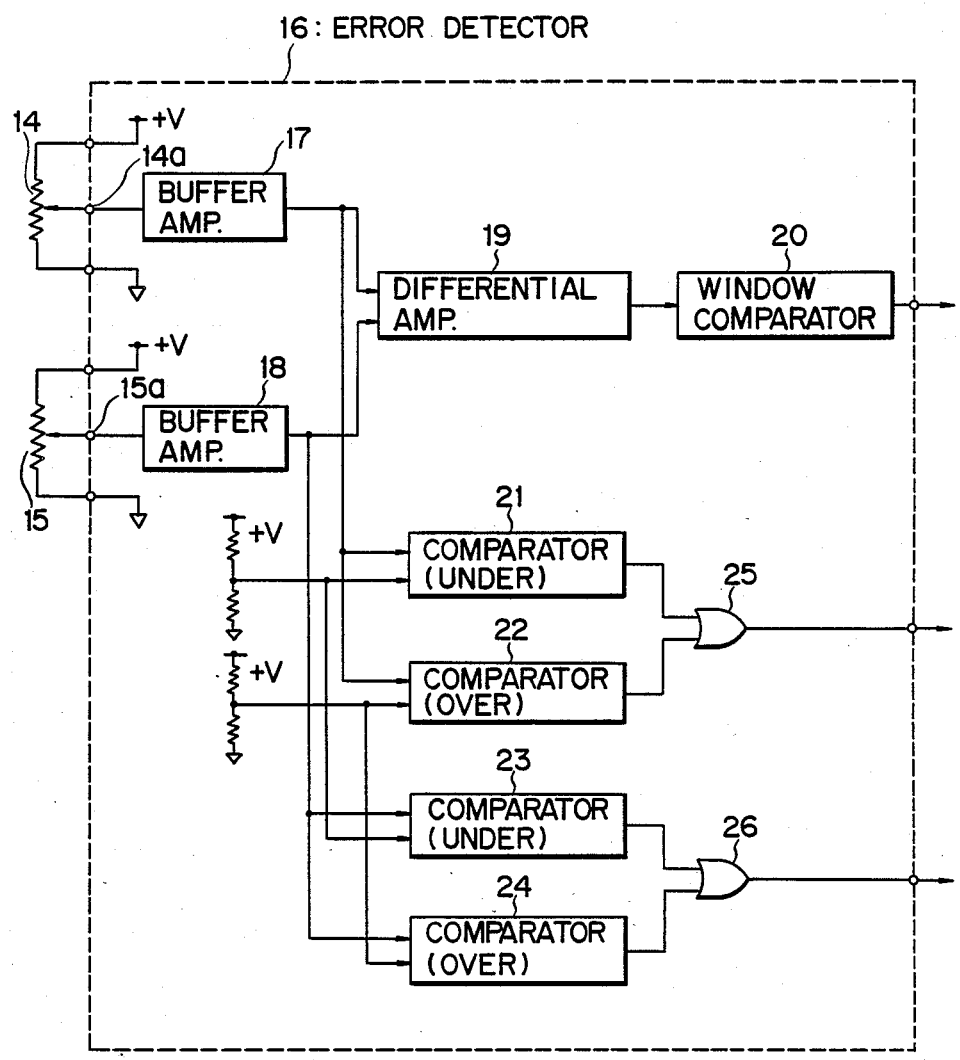
F I G. 3

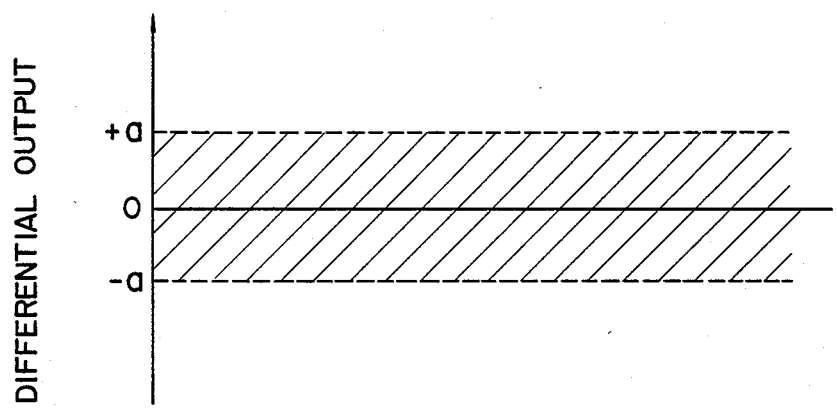
F I G. 4
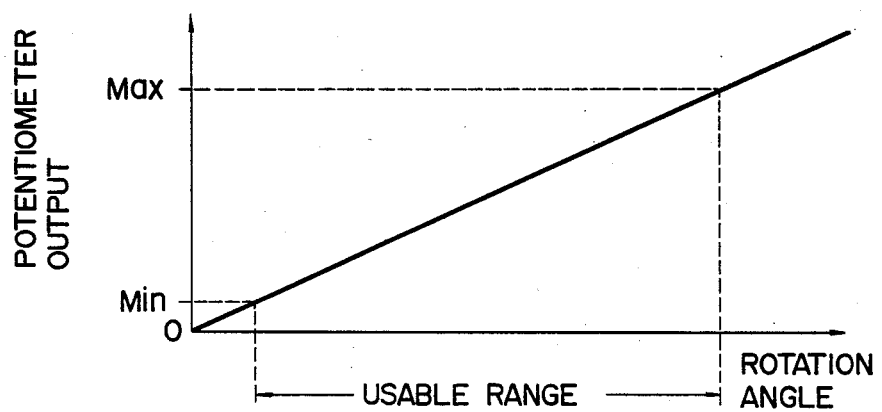
F I G. 5

APPARATUS FOR DETECTING ERROR OF DETECTOR

BACKGROUND OF THE INVENTION

1. Field of the Invention

The present invention relates to an apparatus for detecting an error of a detector and, more particularly, to an apparatus for detecting not only an error of a potentiometer itself for detecting a rotating amount of a rotating body but also a defect of wirings to the potentiometer.

2. Description of the Related Art

An apparatus to which a rotating amount detector is applied is widely used in a variety of technical fields. For example, a case will be explained below wherein the rotating amount detector is applied to an X-ray fluoroscopic imaging system.

The X-ray fluoroscopic imaging system comprises a fluoroscopic X-ray television camera, an image intensifier for converting an X-ray image into an optical image, and an imaging spot shot device. In the fluoroscopic mode, the image intensifier converts an X-ray image of an object to be examined on a top plate of a bed into an optical image, and the optical image is received by the X-ray television camera to be displayed on a CRT (cathode ray tube) display apparatus, or the like.

The top plate of the bed is raisable, and a portion to be examined of an object to which a contrast medium is charged is fluoroscopically observed using the CRT display apparatus by raising the top plate of the bed. When a desired image is obtained, the spot shot device is operated to photograph the image.

FIG. 1 shows an example of the X-ray fluoroscopic imaging system. Referring to FIG. 1, reference numeral 27 denotes a support frame for supporting the entire system; 28, a bed which is raisablly supported by support frame 27; 29, a top plate which is arranged on bed 28 to be movable in a longitudinal direction (A-A+), and on which an object to be examined (patient) lies; and 29a, a step provided at one end of top plate 29. Reference numeral 30 denotes an X-ray tube, which is supported by support arm 31 provided to the side portion in the longitudinal direction of bed 28 to face top plate 29.

Bed 28 incorporates a fluoroscopic imaging system such as an image intensifier, an X-ray television camera, a spot shot device, and the like. The fluoroscopic imaging system is designed to face X-ray tube 30 in synchronism with movement of support arm 31 in directions of arrows D-D'.

In this system, a patient lies on top plate 29 while his feet are placed on step 29a. Bed 28 is then raised in a direction of arrow C to perform X-ray fluoroscopy and imaging.

Top plate 29 is movable in directions of arrows A-A' and B-B' in FIG. 1, so that a desired portion can be placed in an X-ray radiation field. The entire system including bed 28 can be raised in a direction of arrows C-C'. In a standard system, a moving amount of top plate 29 in the direction A-A' is a maximum of 1,000 mm to 1,500 mm, and the raising angle of bed 28 falls within the range of 105 degrees to 180 degrees.

In order to desirably select a portion to be diagnosed, the moving amount of top plate 29 is preferably increased as much as possible. In order to desirably position a contrast medium such as barium in a portion to be diagnosed, the raising angle range is preferably increased as much as possible. Raising angle control of the bed will be explained below. In a conventional system, the rotating shaft of a potentiometer is attached to a rotating shaft of a motor for raising the bed through a decelerator, so that the raising angle of the bed is detected by the potentiometer. If the raising angle of the bed is set at 90 degrees (standing state), the output value from the potentiometer is changed as the raising angle is increased when the raising motor is driven. When the output value has reached a value corresponding to the raising angle of 90 degrees, a raise drive control section detects this fact, and stops rotation of the motor. The raising motion of the bed is stopped at 90 degrees, and the bed is kept in position.

In the conventional system, the raising motion of the bed is controlled by a single potentiometer. Therefore, if the potentiometer is damaged by any cause or if a signal transmission line to the potentiometer is disconnected, an accident may occur. In the above-mentioned raising control of the bed, when the bed overruns without being stopped at the 90-degree position, a patient under examination may suffer from a fatal accident. In moving amount control of the top plate, such an accident may occur due to overrun of the top plate.

SUMMARY OF THE INVENTION

The present invention has been made in consideration of the above situation, and has as its object to provide an error detection apparatus capable of detecting an error when some error occurs in a detector itself or a detection system including its wiring.

An error detection apparatus according to the present invention comprises first and second detectors attached to an object and having identical characteristics, a differential detector for detecting a difference between outputs from the first and second detectors, and an error detector for comparing the difference with a predetermined value and for, when the difference is larger than the predetermined value, generating an error detection signal.

BRIEF DESCRIPTION OF THE DRAWINGS

FIG. 2 is a schematic view of an X-ray fluoroscopic imaging system to which an error detection apparatus according to an embodiment of the present invention is applied;

FIG. 3 is a block diagram showing a circuit arrangement of the error detection apparatus according to the embodiment of the present invention;

FIG. 4 is a graph showing operation characteristics of a window comparator used in the embodiment; and FIG. 5 is a graph showing operation characteristics of a potentiometer used in the embodiment.

DETAILED DESCRIPTION OF THE PREFERRED EMBODIMENT

Figure 1:
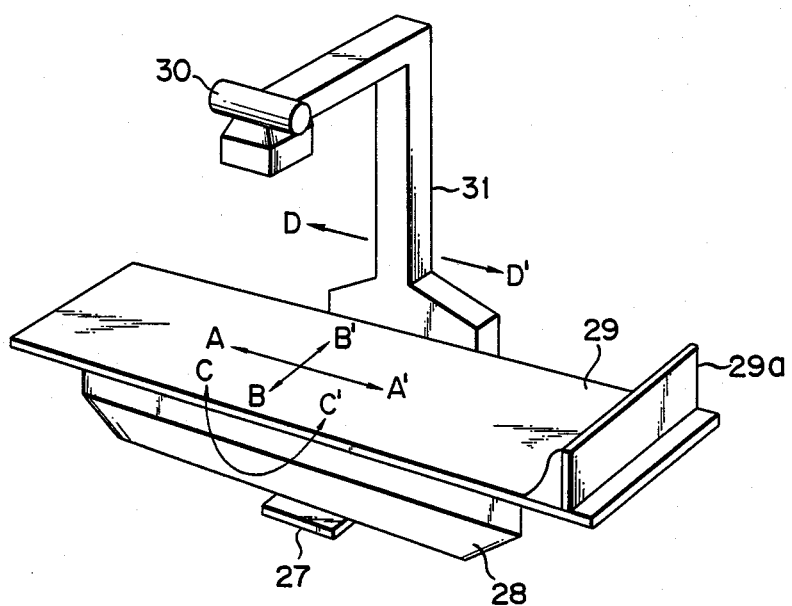
FIG. 1 is a perspective view showing a bed of a conventional X-ray fluoroscopic imaging system.

FIG. 2 shows an embodiment wherein an error detection apparatus of the present invention is applied to a raisable bed of an X-ray fluoroscopic imaging system.

In FIG. 2, reference numeral 1 denotes a bed on which an object to be examined (patient) lies, and which is slidable in a direction of arrows A-A'. In order to facilitate the slide motion of bed 1, guide rollers 3 extending from sector gear 2 engage with guide rail 4 fixed to the upper edge portion of bed 1. Rack 4b is provided to the lower portion of guide rail 4 to extend over the longitudinal direction thereof. Rack 4b is engaged with pinion 6 coaxially provided to rotating shaft 5 of sector gear 2. Rotating shaft 5 of sector gear 2 is rotatably supported by support frame 7. When driving sprocket 8 which is engaged with rack 2a formed on the outer periphery of gear 2 is rotated, sector gear 2 is rotated. Note that the rotating shaft of sprocket 8 is fixed to frame 7. Sprocket 8 is coupled to motor 10 through decelerator 9. Upon normal/reverse rotation of the motor, bed 1 is raised in a direction of arrows C-C'. The rotational force of sprocket 8 is transmitted to pinion 6 by chain 11 through a predetermined decelerator (not shown). Upon rotation of sprocket 8, bed 1 is raised in the direction of arrow C while being slid in the direction of arrow A. This operation is normally called a "rise" operation. Tension roller 12 is arranged on support frame 7 to provide a tension to chain 11.

As the characteristic feature of the present invention, potentiometers having identical characteristics are attached to two rotating portions of the conventional raisable bed described above. First potentiometer 14 is coupled to the rotating shaft of tension roller 12 through decelerator 13, and second potentiometer 15 is coupled to the rotating shaft of second sprocket 8. Decelerator 13 is provided for fine adjustment for precisely coinciding rotating angles of first and second potentiometers 14 and 15 to obtain the identical outputs. The outputs from first and second potentiometers 14 and 15 are input to error detector 16. Then, error detector 16 detects errors of the potentiometers. The potentiometers may be coupled to pinion 6, as a matter of course.

The circuit arrangement of error detector 16 as the characteristic feature of the present invention will be described with reference to FIG. 3.

Movable terminals 14a and 15a of first and second potentiometers 14 and 15, which receive predetermined potential +V [V], are connected to first and second buffer amplifiers 17 and 18. The outputs from these amplifiers are connected to the input terminal of differential amplifier 19. Amplifier 19 detects a difference between the outputs from first and second potentiometers 14 and 15, amplifies the difference, and outputs the amplified difference. The output from differential amplifier 19 is input to window comparator 20. When the output from differential amplifier 19 exceeds an allowable range (+a [V] to −a [V]) indicated by a hatched portion of FIG. 4, comparator 20 outputs an error signal. The output from window comparator 20 is supplied to motor 10 to stop raising bed 1 and an alarm lamp on an operation panel to indicate an error.

The output from buffer amplifier 17 is also connected to first input terminals of minimum and maximum voltage detection comparators 21 and 22. Second input terminals of these comparators 21 and 22 receive different reference voltage values Vmin and Vmax, which are obtained by voltage dividing predetermined potential +V [V] to detect whether or not potentiometer 14 in use is operated in an appropriate usable range shown in FIG. 5. More specifically, when comparator 21 receives a signal lower than reference voltage value Vmin, it outputs a predetermined error signal. When comparator 22 receives a signal higher than reference voltage value Vmax, it outputs a predetermined error signal. The outputs from these comparators 21 and 22 are supplied to OR gate 25. Thus, if one of comparators 21 and 22 outputs the error signal, OR gate 25 outputs an error signal representing an error of first potentiometer 14. The output from OR gate 25 is also supplied to motor 10 and to the alarm lamp on the operation panel in the same manner as that from window comparator 20. The same arrangement for minimum and maximum voltage detection as described above is provided to second potentiometer 15. The output signal of amplifier 18 is similarly supplied to motor 10 and the alarm lamp through comparators 23 and 24, and OR gate 26.

The operation of the X-ray fluoroscopic imaging system described above will be described hereinafter.

When a patient lying on bed 1 must be diagnosed while the bed in a horizontal state is raised to a standing state, an operator designates a standing state (90 degrees) using a predetermined switch on the operation panel. Motor 10 begins to rotate, and bed 1 starts the "rise" operation. During this operation, first potentiometer 14 for detecting rotation of tension roller 12 and second potentiometer 15 for detecting rotation of sprocket 8 gradually increase their output values in the same manner if the system is normal. However, assume that some trouble occurs during the operation, and first potentiometer 14 stops rotating. Thus, a difference is generated between the outputs from first and second potentiometers 14 and 15, and is increased as the raising angle of bed 1 is increased. When the difference exceeds an allowable range shown in FIG. 4, window comparator 20 detects this state, and supplies a predetermined error signal to motor 10 and the alarm lamp on the operation panel. Thus, the "rise" operation of bed 1 is stopped, and the alarm lamp signals an error of the potentiometer. In this manner, the operator can know the error of the potentiometer, and can repair it.

The above-mentioned error occurs during the "rise" operation. In practice, disconnection or short-circuiting may have occurred before the "rise" operation is started. More specifically, in FIG. 3, any of a predetermined potential +V [V] path, a movable terminal path, and an earth potential path may be disconnected or these paths may be short-circuited. Such an error occurs in one potentiometer during the "rise" operation, it can be detected by the circuit system of differential amplifier 19 and window comparator 20. However, if the above error occurs in both first and second potentiometers 14 and 15, it cannot be detected by the above circuit system. Therefore, the circuit system of the minimum and maximum voltage detection comparators allows detection of such an error. That is, when no signal is output from first and second potentiometers 14 and 15 although bed 1 is being raised, an error is detected by minimum voltage detection comparators 21 and 23, and an error signal is output through OR gates 25 and 26. In this case, motor 10 is also stopped, and the alarm lamp on the operation panel is turned on, thereby signaling the error of the potentiometer to the operator. With these comparators, when one potentiometer is disconnected or short-circuited during the "rise" operation, it can be detected which potentiometer malfunctions.

According to the detector of this embodiment, if any error of potentiometers occurs, it can be reliably detected, and drive control and an alarm to an operator can be achieved. Therefore, in an X-ray fluoroscopic imaging system which must have safety as its primary importance, extremely great advantages can be provided.

The present invention is not limited to the above embodiment, and various changes and modifications may be made within the spirit and scope of the invention. For example, the error detector in the above embodiment is designed to process an analog signal. Instead, the error detector may be designed to process a digital signal.

More specifically, in FIG. 3, the outputs from buffer amplifiers 17 and 18 are converted into digital signals by an A/D converter, and the digital signals are input to a CPU (Central Processing Unit). The CPU then executes a difference detection, and minimum/maximum voltage detection to output a predetermined error signal in the same manner as in the embodiment shown in FIG. 2. In this manner, if an error is detected by a digital circuit system, the circuit system is not easily affected by an external noise component, a difference between two potentiometers can be more precisely detected. In addition, an arrangement can be simplified. In this modification, if rotary encoders are used i place of potentiometers 14 and 15, no A/D converter is required, and the arrangement can be further simplified. Moreover, according to this modification, fine correction of rotational angles for coinciding outputs from first and second rotary encoders may be performed by the CPU. More specifically, the characteristic feature of the present invention is that a plurality of detectors of the same characteristic are provided to identical objects. In this sense, the outputs from these detectors must coincide with each other. For this purpose, in the embodiment shown in FIG. 2, the rotational angles of potentiometers are finely adjusted using decelerator 13, so that the outputs from potentiometers 14 and 15 coincide with each other. If the outputs are numerically compensated by the CPU, it can be achieved with higher precision than that by decelerator 13.

In the above description, two potentiometers serving as detectors connected to tension roller 12 and sprocket 8 are arranged. However, the number of connections is not limited to this. If identical detection values are obtained, the potentiometers may be connected to any portions. The number of potentiometers is not limited to two but may be three or more. If the number of potentiometers is increased more than 3, the numbers of buffer amplifiers 17 or 18 and differential amplifiers 19, and those of minimum and maximum voltage detection comparators 21 and 22 or 23 and 24 need only be increased. The detector is not limited to the potentiometer. Window comparator 20 may be replaced by a combination of maximum and minimum detection comparators. Similarly, maximum and minimum detection comparators 21, 22; 23, 24 may be replaced by a window comparator. The present invention can be widely applied to normal detectors. In addition, the present invention is not limited to an X-ray fluoroscopic imaging system.

What is claimed is:

1. A control apparatus for a raisable bed of an X-ray fluoroscopic imaging system, comprising:
    a first gear provided to a side portion of said bed;
    a rack provided in a longitudinal direction of said bed;
    a pinion, meshed with said rack, for moving said bed in a horizontal direction;
    a second gear meshed with said first gear, for raising said bed;
    a motor for integrally rotating said pinion and said second gear through a power transmission means so as to raise said bed;
    first and second potentiometers, which are connected to two rotating shafts of said pinion and said second gear, and have identical detection characteristics, for detecting rotational angles of said two rotating shafts;
    means for detecting a difference between outputs from said first and second potentiometers; and
    first means for comparing the difference with a predetermined value and for, when the difference is larger than the predetermined value, generating a first error detection signal representing an error of at least one of said first and second potentiometers.

2. An apparatus according to claim 1, further comprising:
    means for stopping rotation of said motor when the first error signal is generated.

3. An apparatus according to claim 1, in which said motor rotates said pinion and said second gear through said power transmission means and further through a tension idler and in which said first and second potentiometers are connected to two rotating shafts of said pinion, said second gear, and said tension idler.

4. An apparatus according to claim 1, in which one of said first and second potentiometers is connected to any rotating shaft of said pinion and said and second gear through a decelerator.

5. An apparatus according to claim 1, in which said first means for comparing comprises a window comparator.

6. An apparatus according to claim 1, further comprising:
    second means for comparing the output from said first potentiometer with upper and lower limits of a rise angle of said bed, and for, when the output is larger than the upper limit or smaller than the lower limit of the rise angle, generating a second error signal representing an error of said first potentiometer; and
    third means for comparing the output from said second potentiometer with the upper and lower limits of the rise angle of said bed, and for, when the output is larger than the upper limit or smaller than the lower limit of the rise angle, generating a third error signal representing an error of said second potentiometer.

7. An apparatus according to claim 6, further comprising:
    means for stopping rotation of said motor when the second or third error signal is generated.

8. An apparatus according to claim 6, in which said second and third means for comparing comprise a window comparator.

* * * * *